(12) United States Patent
Yamaguchi et al.

(10) Patent No.: US 12,023,398 B2
(45) Date of Patent: Jul. 2, 2024

(54) COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

(71) Applicant: RICOH COMPANY, LTD., Tokyo (JP)

(72) Inventors: Tatsuki Yamaguchi, Kanagawa (JP); Masahide Kobayashi, Kanagawa (JP); Mitsunobu Morita, Shizuoka (JP); Takashi Okada, Kanagawa (JP); Soh Noguchi, Kanagawa (JP); Takenori Suenaga, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 663 days.

(21) Appl. No.: 17/264,200

(22) PCT Filed: Jul. 1, 2019

(86) PCT No.: PCT/JP2019/026152
§ 371 (c)(1),
(2) Date: Jan. 28, 2021

(87) PCT Pub. No.: WO2020/026675
PCT Pub. Date: Feb. 6, 2020

(65) Prior Publication Data
US 2021/0309771 A1  Oct. 7, 2021

(30) Foreign Application Priority Data

Jul. 31, 2018 (JP) .................. 2018-143430
May 8, 2019 (JP) .................. 2019-087984

(51) Int. Cl.
| | | |
|---|---|---|
| *A61K 8/42* | (2006.01) | |
| *A45D 29/00* | (2006.01) | |
| *A45D 31/00* | (2006.01) | |
| *A61K 8/37* | (2006.01) | |
| *A61K 8/81* | (2006.01) | |
| *A61Q 3/00* | (2006.01) | |
| *A61Q 3/02* | (2006.01) | |
| *C08F 2/48* | (2006.01) | |
| *C08F 2/50* | (2006.01) | |
| *C08F 20/56* | (2006.01) | |
| *C08F 220/58* | (2006.01) | |
| *C09D 4/00* | (2006.01) | |
| *G03C 1/73* | (2006.01) | |
| *G03C 1/74* | (2006.01) | |

(52) U.S. Cl.
CPC .............. *A61K 8/42* (2013.01); *A45D 31/00* (2013.01); *A61K 8/375* (2013.01); *A61K 8/8141* (2013.01); *A61K 8/8158* (2013.01); *A61K 8/8194* (2013.01); *A61Q 3/00* (2013.01); *A61Q 3/02* (2013.01); *C08F 2/48* (2013.01); *C08F 2/50* (2013.01); *C08F 20/56* (2013.01); *C08F 220/58* (2013.01); *C09D 4/00* (2013.01); *G03C 1/73* (2013.01); *G03C 1/74* (2013.01); *A45D 2029/005* (2013.01); *A45D 2200/205* (2013.01); *A61K 2800/81* (2013.01); *A61K 2800/87* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 4,690,369 A | 9/1987 | Giuliano | |
| 10,174,215 B2 | 1/2019 | Morita et al. | |
| 11,059,985 B2 * | 7/2021 | Kobayashi | ............. B41J 11/002 |
| 11,084,940 B2 * | 8/2021 | Yamaguchi | ............ B33Y 30/00 |
| 2009/0286435 A1 | 11/2009 | Badyal et al. | |
| 2014/0363634 A1 | 12/2014 | Morita et al. | |
| 2015/0077481 A1 | 3/2015 | Yoshino et al. | |
| 2015/0232675 A1 | 8/2015 | Yoshino et al. | |
| 2016/0088919 A1 | 3/2016 | Oohashi | |
| 2017/0137644 A1 | 5/2017 | Morita et al. | |
| 2017/0253680 A1 | 9/2017 | Yamada | |
| 2017/0260405 A1 | 9/2017 | Kumai et al. | |
| 2017/0327705 A1 | 11/2017 | Yamada | |
| 2018/0036559 A1 | 2/2018 | Ishiji et al. | |
| 2018/0049966 A1 | 2/2018 | Ishiji et al. | |
| 2018/0127607 A1 | 5/2018 | Morita et al. | |
| 2018/0244831 A1 | 8/2018 | Hirata et al. | |
| 2018/0244832 A1 | 8/2018 | Takenouchi et al. | |
| 2018/0333909 A1 | 11/2018 | Arita et al. | |

(Continued)

FOREIGN PATENT DOCUMENTS

| | | |
|---|---|---|
| CN | 104231744 A | 12/2014 |
| EP | 3321333 A1 | 5/2018 |

(Continued)

OTHER PUBLICATIONS

English abstract for JP 2013-43853A (Year: 2013).*

(Continued)

*Primary Examiner* — Sin J Lee
(74) *Attorney, Agent, or Firm* — Grüneberg and Myers PLLC

(57) ABSTRACT

Provided is a composition including: an acrylamide compound (A1) having a molecular weight of 150 or greater but 250 or less; and a multifunctional polymerizable compound (A2), wherein a content of the multifunctional polymerizable compound (A2) is 15% by mass or greater but 35% by mass or less.

11 Claims, 3 Drawing Sheets

(56) References Cited

U.S. PATENT DOCUMENTS

2019/0023924 A1  1/2019  Yamada
2019/0023941 A1  1/2019  Ford et al.
2019/0031902 A1* 1/2019  Kotani ................ B41M 5/0023

FOREIGN PATENT DOCUMENTS

| | | |
|---|---|---|
| EP | 3431557 A1 | 1/2019 |
| JP | 2009-126833 A | 6/2009 |
| JP | 2013-043853 | 3/2013 |
| JP | 2015-083656 | 4/2015 |
| JP | 2015-189668 | 11/2015 |
| JP | 2017-206674 | 11/2017 |
| JP | 2018-080321 | 5/2018 |
| JP | 2019-085330 | 6/2019 |
| WO | WO2006/109055 A2 | 10/2006 |
| WO | WO2014/199966 A1 | 12/2014 |
| WO | WO2016/194730 A1 | 12/2016 |
| WO | WO2017/014975 A1 | 1/2017 |
| WO | WO2017/047565 A1 | 3/2017 |
| WO | WO2017/047615 A1 | 3/2017 |
| WO | WO2018/198692 A1 | 11/2018 |

OTHER PUBLICATIONS

English translation for JP 2013-43853A (Year: 2013).*
International Search Report Issued Sep. 11, 2019 for counterpart International Patent Application No. PCT/JP2019/026152 filed Jul. 1, 2019.
Written Opinion Issued Sep. 11, 2019 for counterpart International Patent Application No. PCT/JP2019/026152 filed Jul. 1, 2019.
PCT Collaborative Search and Examination Pilot Peer Contribution uploaded Aug. 13, 2019 by the JPO which is a peer ISA for counterpart International Patent Application No. PCT/JP2019/026152 filed Jul. 1, 2019.
PCT Collaborative Search and Examination Pilot Peer Contribution uploaded Aug. 15, 2019 by the CNIPA which is a peer ISA for counterpart Additional References sheet(s) attached International Patent Application No. PCT/JP2019/026152 filed Jul. 1, 2019.
PCT Collaborative Search and Examination Pilot Peer Contribution uploaded Aug. 30, 2019 by the KIPO which is a peer ISA for counterpart International Patent Application No. PCT/JP2019/026152 filed Jul. 1, 2019.

* cited by examiner

[Fig. 1]
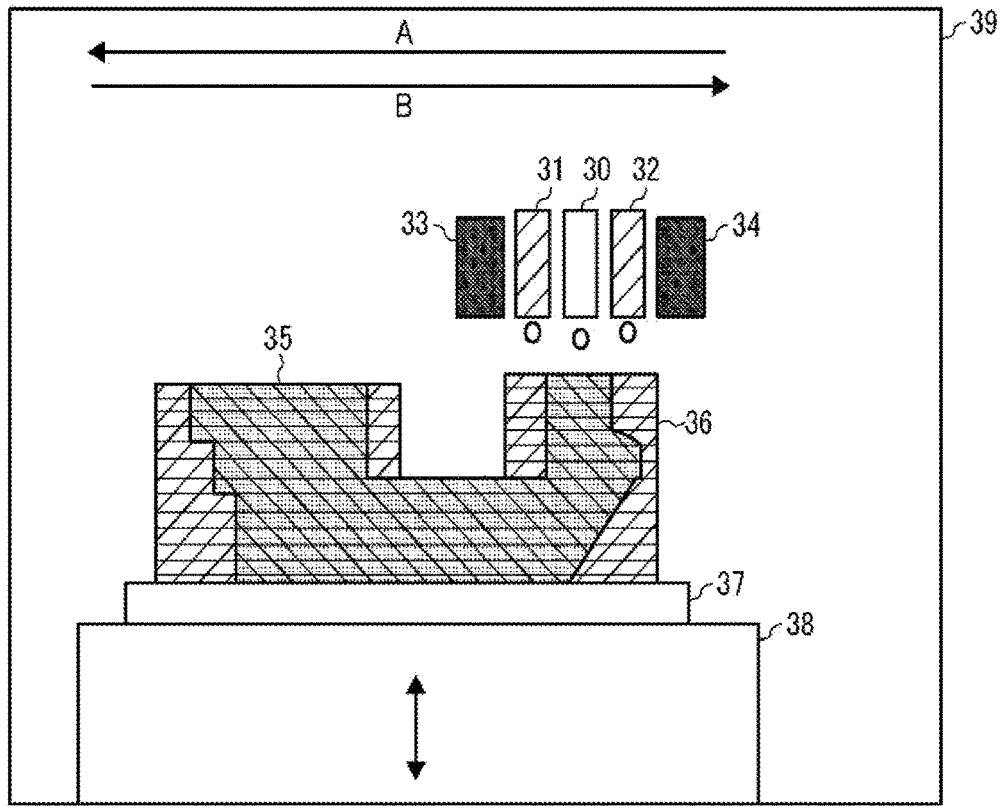
[Fig. 2A]
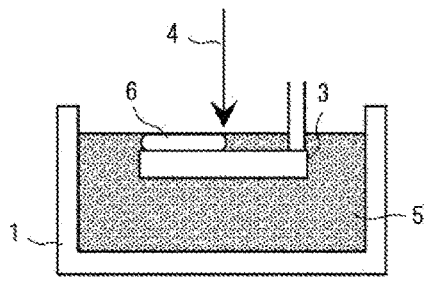
[Fig. 2B]
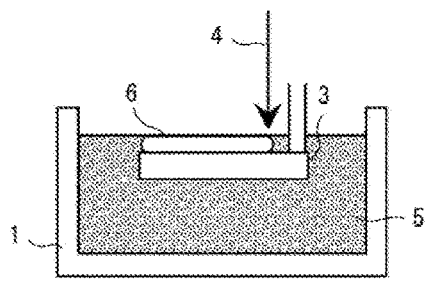
[Fig. 2C]
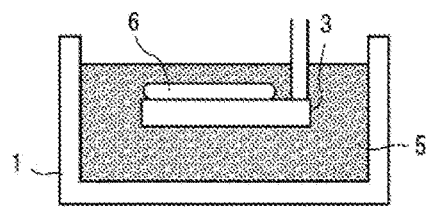

[Fig. 2D]
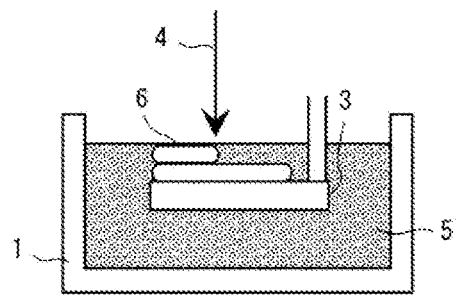
[Fig. 3A]
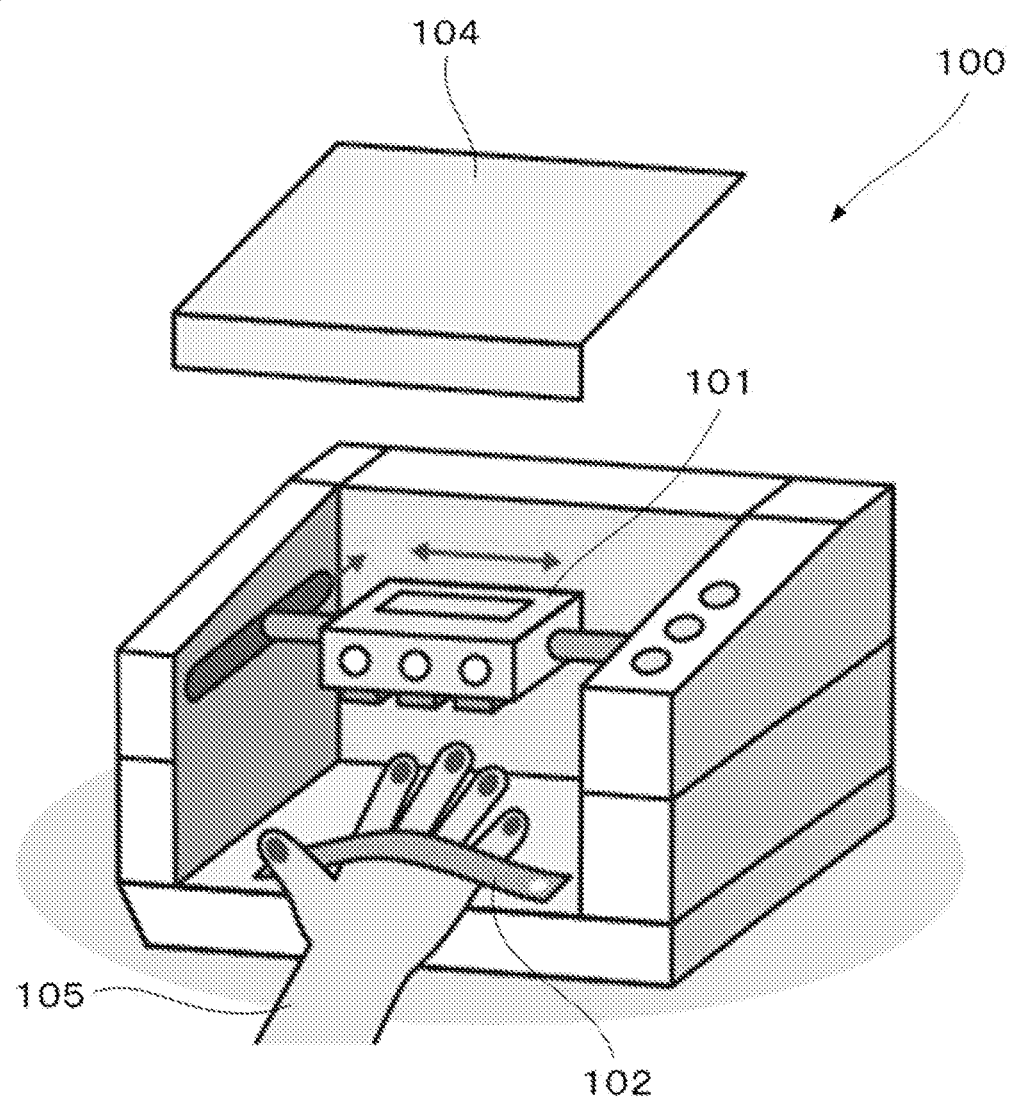

[Fig. 3B]
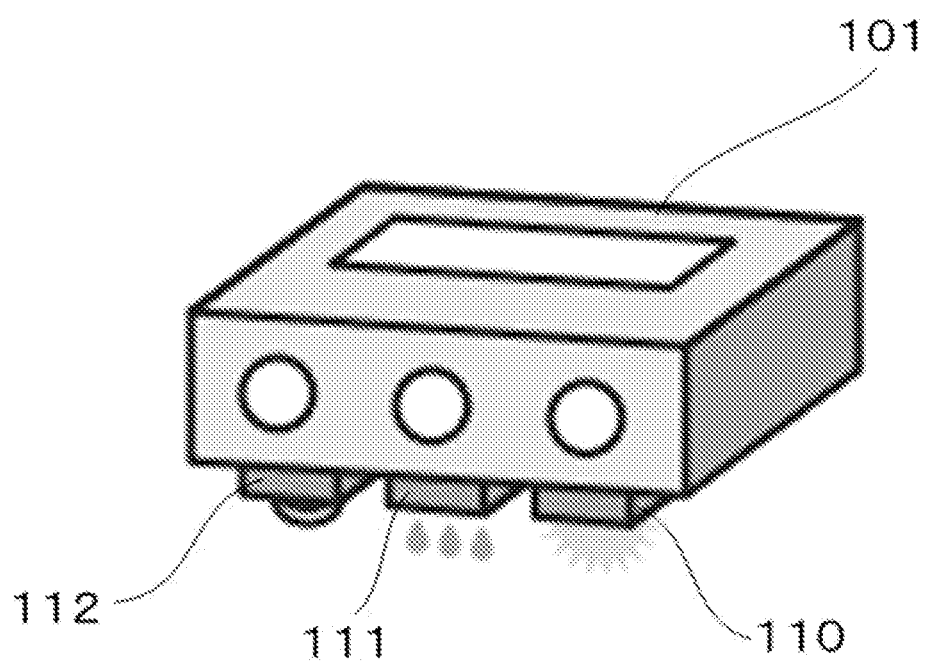

COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

TECHNICAL FIELD

The present disclosure relates to a composition, an artificial nail composition, a nail decoration material, an artificial nail, a stored container, an image forming apparatus, and an image forming method.

BACKGROUND ART

Nail art using gel nail materials needs close adhesiveness with nails in order to be prevented from being easily peeled in daily life. On the other hand, when removing nail art, it is common to leave to stand over the nail art, a wipe or cotton impregnated with a solution called a nail remover containing an organic solvent such as acetone as a main component, to swell and remove the nail art.

However, artificial nails excellent in close adhesiveness with nails typically have a cross-linked structure and hence an excellent solvent resistance. Therefore, such artificial nails are difficult to remove by the method described above. Hence, for removing artificial nails, there is a need for scraping off the artificial nails by sanding or mechanically removing the artificial nails using a nail machine.

In order to bring improvement to this circumstance, for example, there has been proposed an artificial nail coating composition in which a urethane bond-containing photopolymerizable compound is blended to have improved removability (for example, see PTL 1).

There has also been proposed an artificial nail composition containing an ionic monomer polymerizable by ultraviolet irradiation in the composition and removable with an acidic aqueous solution (for example, see PTL 2).

CITATION LIST

Patent Literature

PTL 1: Japanese Unexamined Patent Application Publication No. 2015-189668
PTL 2: Japanese Unexamined Patent Application Publication No. 2009-126833

SUMMARY OF INVENTION

Technical Problem

The present disclosure has an object to provide a composition that, when used as an artificial nail composition, can provide a cured product excellent in close adhesiveness with nails and having a safe removability.

Solution to Problem

According to one aspect of the present disclosure, a composition contains an acrylamide compound (A1) having a molecular weight of 150 or greater but 250 or less and a multifunctional polymerizable compound (A2). The content of the multifunctional polymerizable compound (A2) is 15% by mass or greater but 35% by mass or less.

Advantageous Effects of Invention

The present disclosure can provide a composition that, when used as an artificial nail composition, can provide a cured product (artificial nail) excellent in close adhesiveness with nails and having a safe removability.

BRIEF DESCRIPTION OF DRAWINGS

FIG. 1 is a schematic view illustrating an example of another image forming apparatus (three-dimensional stereoscopic image forming apparatus).
FIG. 2A is a schematic view illustrating an example of a method for forming a three-dimensional object using a composition.
FIG. 2B is a schematic view illustrating an example of a method for forming a three-dimensional object using a composition.
FIG. 2C is a schematic view illustrating an example of a method for forming a three-dimensional object using a composition.
FIG. 2D is a schematic view illustrating an example of a method for forming a three-dimensional object using a composition.
FIG. 3A is a schematic view illustrating an example of a nail decorating apparatus configured to decorate a human nail.
FIG. 3B is an enlarged schematic view of a decorating unit of FIG. 3A.

DESCRIPTION OF EMBODIMENTS (Composition)

A composition of the present disclosure contains an acrylamide compound (A1) having a molecular weight of 150 or greater but 250 or less and a multifunctional polymerizable compound (A2). The content of the multifunctional polymerizable compound (A2) is 15% by mass or greater but 35% by mass or less. The composition further contains other components as needed.

The composition of the present disclosure is based on a finding that the existing technique of Japanese Unexamined Patent Application Publication No. 2015-189668 needs mechanical removal because the crosslink density may be high depending on the amount of the urethane bond-containing photopolymerizable compound blended.

The composition of the present disclosure is also based on a finding that the existing technique of Japanese Unexamined Patent Application Publication No. 2009-126833 has a risk of damaging nails or skin because the technique employs removal with an acidic aqueous solution having pH of 3.5 or lower.

The composition of the present disclosure contains an acrylamide compound (A1) having a molecular weight of 150 or greater but 250 or less and a multifunctional polymerizable compound (A2), and the content of the multifunctional polymerizable compound (A2) is 15% by mass or greater but 35% by mass or less. Hence, when used as an artificial nail composition, the composition is excellent in close adhesiveness with nails and removability, and suitable as a base coat for an artificial nail composition.

The composition of the present disclosure is preferably a curable composition. Examples of the curable composition include thermosetting compositions and active-energy-ray-curable compositions. Active-energy-ray-curable compositions are more preferable.

<Acrylamide Compound (A1)>

The acrylamide compound (A1) contains an acrylamide group and an ester structure, and has a molecular weight of 150 or greater but 250 or less.

The molecular weight of the acrylamide compound (A1) is 150 or greater but 250 or less, and preferably 150 or greater but 200 or less. It is preferable that the molecular weight of the acrylamide compound (A1) be 150 or greater, because odor due to volatilization of the compound can be suppressed, and inkjet discharging stability can be improved. It is preferable that the molecular weight of the acrylamide compound (A1) be 250 or less, because the composition has an excellent curability, a cured product of the composition has an improved strength, and the viscosity of the composition is not high.

As used herein, (meth)acrylic acid ester refers to acrylic acid ester or methacrylic acid ester, and (meth)acrylate refers to acrylate or methacrylate.

The acrylamide compound (A1) is preferably a compound represented by at least any one selected from the group consisting of general formulae (1) and (2) below, more preferably a compound represented by any one selected from the group consisting of general formulae (1) and (2) below, and yet more preferably a compound represented by general formula (1) below.

[Chem. 1]

General formula (1)

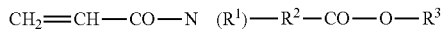

In general formula (1), $R^1$ represents a hydrogen atom, or a straight-chain or branched alkyl group containing 1 through 4 carbon atoms, and preferably represents a straight-chain or branched alkyl group containing 1 through 4 carbon atoms. Examples of $R^1$ include a methyl group, an ethyl group, a propyl group, an isopropyl group, a butyl group, a sec-butyl group, an isobutyl group, and a tert-butyl group. In general formula (1), $R^2$ represents a straight-chain or branched alkylene group containing 1 through 4 carbon atoms. Examples of $R^2$ include a methylene group, an ethane-1,1-diyl group, an ethane-1,2-diyl group, a propane-1,1-diyl group, a propane-1,2-diyl group, a propane-1,3-diyl group, a butane-1,1-diyl group, a butane-1,2-diyl group, a butane-1,3-diyl group, a butane-1,4-diyl group, a 2-methyl propane-1,1-diyl group, a 2-methyl propane-1,2-diyl group, and a 2-methyl propane-1,3-diyl group. In general formula (1), $R^3$ represents a straight-chain or branched alkyl group containing 1 through 4 carbon atoms. Examples of $R^3$ include a methyl group, an ethyl group, a propyl group, an isopropyl group, a butyl group, a sec-butyl group, an isobutyl group, and a tert-butyl group.

The total number of carbon atoms in $R^1$, $R^2$, and $R^3$ is 2 through 6.

[Chem. 2]

General formula (2)

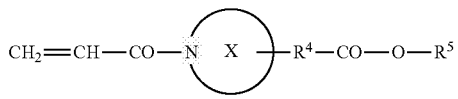

In general formula (2), the ring X represents a nitrogen atom-containing ring structure containing 2 through 5 carbon atoms. Examples of the ring X include aziridine, azetidine, pyrrolidine, and piperidine. The ring X is preferably pyrrolidine or piperidine.

In general formula (2), $R^4$ represents a single bond, or a straight-chain or branched alkylene group containing 1 through 3 carbon atoms. Examples of $R^4$ include a single bond, a methylene group, an ethane-1,1-diyl group, an ethane-1,2-diyl group, a propane-1,1-diyl group, a propane-1,2-diyl group, and a propane-1,3-diyl group.

In general formula (2), $R^5$ represents a straight-chain or branched alkyl group containing 1 through 3 carbon atoms. Examples of $R^5$ include a methyl group, an ethyl group, a propyl group, and an isopropyl group.

The total number of carbon atoms in the ring X, $R^4$, and $R^5$ is 3 through 6.

As the compound represented by general formula (1) or (2), for example, N-acryloyl-N-alkyl amino acid alkyl ester (including N-acryloyl proline alkyl ester) and N-acryloyl piperidine carboxylic acid alkyl ester are preferable. Alkyl group as used herein refers to a straight-chain or branched alkyl group containing 1 through 4 carbon atoms. Particularly preferable examples of the alkyl group include an alkyl group containing 1 or 2 carbon atoms (i.e., a methyl group or an ethyl group).

The N-acryloyl-N-alkyl amino acid alkyl ester is not particularly limited and may be appropriately selected depending on the intended purpose. Examples of the N-acryloyl-N-alkyl amino acid alkyl ester include N-acryloyl-N-methyl glycine methyl ester, N-acryloyl-N-methyl glycine ethyl ester, N-acryloyl-N-methyl glycine propyl ester, N-acryloyl-N-methyl glycine butyl ester, N-acryloyl-N-ethyl glycine methyl ester, N-acryloyl-N-ethyl glycine ethyl ester, N-acryloyl-N-ethyl glycine propyl ester, N-acryloyl-N-propyl glycine methyl ester, N-acryloyl-N-propyl glycine ethyl ester, N-acryloyl-N-butyl glycine methyl ester, N-acryloyl-N-methyl alanine methyl ester, N-acryloyl-N-methyl alanine ethyl ester, N-acryloyl-N-methyl alanine propyl ester, N-acryloyl-N-ethyl alanine methyl ester, N-acryloyl-N-ethyl alanine ethyl ester, N-acryloyl-N-propyl alanine methyl ester, N-acryloyl-N-methyl-β-alanine methyl ester, N-acryloyl-N-methyl-β-alanine ethyl ester, N-acryloyl-N-ethyl-β-alanine methyl ester, N-acryloyl-N-ethyl-β-alanine ethyl ester, N-acryloyl-N-methyl valine methyl ester, N-acryloyl proline methyl ester, and N-acryloyl proline ethyl ester. One of these N-acryloyl-N-alkyl amino acid alkyl esters may be used alone or two or more of these N-acryloyl-N-alkyl amino acid alkyl esters may be used in combination.

The N-acryloyl piperidine carboxylic acid alkyl ester is not particularly limited and may be appropriately selected depending on the intended purpose. Examples of the N-acryloyl piperidine carboxylic acid alkyl ester include methyl N-acryloyl piperidine-2-carboxylate, methyl N-acryloyl piperidine-3-carboxylate, and methyl N-acryloyl piperidine-4-carboxylate. One of these N-acryloyl piperidine carboxylic acid alkyl esters may be used alone or two or more of these N-acryloyl piperidine carboxylic acid alkyl esters may be used in combination.

For application to an inkjet recording method, it is preferable that the acrylamide compound (A1) be a colorless transparent, or pale-yellow transparent liquid having a low viscosity (100 mPa·s or lower) at normal temperature (25 degrees C.). For safety of the user, it is preferable that the acrylamide compound (A1) not be strongly acidic or basic, and be free of toxic formaldehyde as an impurity.

The content of the acrylamide compound (A1) is preferably 20% by mass or greater but 80% by mass or less, more preferably 40% by mass or greater but 75% by mass or less, and yet more preferably 64.8% by mass or greater but 75% by mass or less relative to the total amount of the composition.

<Multifunctional Polymerizable Compound (A2)>

The multifunctional polymerizable compound (A2) is not particularly limited, may be appropriately selected depending on the intended purpose, and is preferably bifunctional or greater but hexafunctional or less.

Examples of the multifunctional polymerizable compound (A2) include bisphenol A-propylene oxide (PO) adduct di(meth)acrylate, ethoxylated neopentyl glycol di(meth)acrylate, propoxylated neopentyl glycol di(meth) acrylate, polyethylene glycol di(meth)acrylate, polypropylene glycol di(meth)acrylate, bisphenol A-ethylene oxide (EO) adduct di(meth)acrylate, EO-modified pentaerythritol tri(meth)acrylate, PO-modified pentaerythritol tri(meth) acrylate, EO-modified pentaerythritol tetra(meth)acrylate, PO-modified pentaerythritol tetra(meth)acrylate, EO-modified dipentaerythritol tetra(meth)acrylate, PO-modified dipentaerythritol tetra(meth)acrylate, EO-modified trimethylolpropane tri(meth)acrylate, PO-modified trimethylolpropane tri(meth)acrylate, EO-modified tetramethylolmethane tetra(meth)acrylate, PO-modified tetramethylolmethane tetra(meth)acrylate, caprolactone-modified dipentaerythritol hexa(meth)acrylate, pentaerythritol tri(meth)acrylate, pentaerythritol tetra(meth)acrylate, dipentaerythritol tetra(meth) acrylate, trimethylolpropane tri(meth)acrylate, tetramethylolmethane tetra(meth)acrylate, trimethylolethane tri(meth) acrylate, trimethylolpropane tri(meth)acrylate, bis(4-(meth) acryloxypolyethoxyphenyl)propane, diallyl phthalate, triallyl trimellitate, 1,6-hexanediol di(meth)acrylate, 1,9-nonanediol di(meth)acrylate, 1,3-butylene glycol di(meth) acrylate, 1,10-decanediol di(meth)acrylate, hydroxypivalic acid neopentyl glycol di(meth)acrylate, tetramethylolmethane tri(meth)acrylate, dimethylol tricyclodecane di(meth) acrylate, modified glycerin tri(meth)acrylate, bisphenol A-diglycidyl ether (meth)acrylic acid adduct, modified bisphenol A di(meth)acrylate, dipentaerythritol hexa(meth) acrylate, pentaerythritol tri(meth)acrylate tolylene diisocyanate urethane prepolymer, pentaerythritol tri(meth)acrylate hexamethylene diisocyanate urethane prepolymer, ditrimethylolpropane tetra(meth)acrylate, and pentaerythritol tri (meth)acrylate hexamethylene diisocyanate urethane prepolymer. One of these multifunctional polymerizable compounds may be used alone or two or more of these multifunctional polymerizable compounds may be used in combination.

As the multifunctional polymerizable compound (A2), a multifunctional oligomer may be used. The multifunctional oligomer is not particularly limited and may be appropriately selected depending on the intended purpose. Urethane oligomer is preferable.

As the urethane oligomer, a commercially available product may be used. Examples of the commercially available product include: UV-2000B, UV-2750B, UV-3000B, UV-3010B, UV-3200B, UV-3300B, UV-3700B, UV-6640B, UV-8630B, UV-7000B, UV-7610B, UV-1700B, UV-7630B, UV-6300B, UV-6640B, UV-7550B, UV-7600B, UV-7605B, UV-7610B, UV-7630B, UV-7640B, UV-7650B, UT-5449, and UT-5454 available from Nippon Synthetic Chemical Industry Co., Ltd.; CN929, CN961E75, CN961H81, CN962, CN963, CN963A80, CN963B80, CN963E75, CN963E80, CN963J85, CN965, CN965A80, CN966A80, CN966H90, CN966J75, CN968, CN981, CN981A75, CN981B88, CN982, CN982A75, CN982B88, CN982E75, CN983, CN985B88, CN9001, CN9002, CN9788, CN970A60, CN970E60, CN971, CN971A80, CN972, CN973A80, CN973H85, CN973J75, CN975, CN977C70, CN978, CN9782, CN9783, CN996, and CN9893 available from Sartomer Company Inc.; and EBECRYL210, EBECRYL220, EBECRYL230, EBECRYL270, KRM8200, EBECRYL5129, EBECRYL8210, EBECRYL8301, EBECRYL8804, EBECRYL8807, EBECRYL9260, KRM7735, KRM8296, KRM8452, EBECRYL4858, EBECRYL8402, EBECRYL9270, EBECRYL8311, and EBECRYL8701 available from Daicel Cytec Co., Ltd. One of these commercially available products may be used alone or two or more of these commercially available product may be used in combination.

The content of the multifunctional polymerizable compound (A2) is 15% by mass or greater but 35% by mass or less and preferably 15% by mass or greater but 20% by mass or less relative to the total amount of the composition. When the content of the multifunctional polymerizable compound (A2) is 15% by mass or greater but 35% by mass or less, a cured product (artificial nail) excellent in removability and close adhesiveness with nails can be obtained. When there are a plurality of multifunctional polymerizable compounds (A2), the total content of all such multifunctional polymerizable compounds (A2) is 15% by mass or greater but 35% by mass or less and preferably 15% by mass or greater but 20% by mass or less relative to the total amount of the composition.

When the content of the multifunctional polymerizable compound (A2) is less than 15% by mass, a cured product has a relatively low crosslink density and hence an insufficient solvent resistance. Therefore, the cured product dissolves in an organic solvent used during removal, raising a risk of direct contact of the organic solvent with nails or skin, which may hence be chemically injured. On the other hand, when the content of the multifunctional polymerizable compound (A2) is greater than 35% by mass, the cured product has a relatively high crosslink density and hence an improved solvent resistance, which may be of a level difficult for the cured product to be removed with an organic solvent. Moreover, the multifunctional polymerizable compound (A2) in a high content causes a relatively great volume shrinkage during curing. Therefore, the cured product may have a poor close adhesiveness with nails.

The solubility parameter (SP value) of the multifunctional polymerizable compound (A2) alone is preferably 10 (cal/cm$^3$)$^{0.5}$ or less in terms of solvent resistance and water resistance. The SP value can be calculated according to Fedors method (see R. F. Fedors: Polym. Eng. Sci., 14 [2], pp. 147-154 (1974)).

Examples of the multifunctional polymerizable compound having a SP value of 10 or less include dipentaerythritol hexa(meth)acrylate (SP value: 8.2), caprolactone-modified dipentaerythritol hexa(meth)acrylate (SP value: 9.8), pentaerythritol tetra(meth)acrylate (SP value: 8.5), and diethylene glycol di(meth)acrylate (SP value: 8.9).

<Other Polymerizable Compounds than Acrylamide Compound Represented (A1) and Multifunctional Polymerizable Compound (A2)>

The composition of the present disclosure may contain other polymerizable compounds than the acrylamide compound (A1) and the multifunctional polymerizable compound (A2).

As other polymerizable compounds, known polymerizable monomers, of which representative examples are (meth)acrylic acid esters, can be used. Examples of other polymerizable compounds include methyl (meth)acrylate, ethyl (meth)acrylate, n-butyl (meth)acrylate, allyl(meth) acrylate, glycidyl (meth)acrylate, 2-(dimethylamino)ethyl (meth)acrylate, 2-hydroxyethyl (meth)acrylate, 2-butoxyethyl (meth)acrylate, ethyl carbitol (meth)acrylate, cyclohexyl (meth)acrylate, tetrahydrofurfuryl (meth)acrylate, 2-(2-vinyloxyethoxy)ethyl (meth)acrylate, benzyl (meth) acrylate, 2-phenoxyethyl (meth)acrylate, 2-hydroxy-3-phenoxypropyl (meth)acrylate, isobornyl (meth)acrylate, ethylene glycol di(meth)acrylate, diethylene glycol di(meth) acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, neopentyl glycol di(meth)acrylate, ethoxylated neopentyl glycol di(meth)acrylate, propoxylated neopentyl glycol di(meth)acrylate, 1,6-hexanediol di(meth)acrylate, and 1,9-nonanediol di(meth)acrylate. One of these other polymerizable compounds may be used alone or two or more of these other polymerizable compounds may be used in combination.

Further examples of other polymerizable compounds include urethane (meth)acrylate derivatives obtained by allowing a hydroxyl group-containing (meth)acrylic acid ester to undergo reaction with an isocyanate group-containing compound and epoxy (meth)acrylate derivatives obtained by allowing (meth)acrylic acid to undergo reaction with an epoxy group-containing compound.

In addition to (meth)acrylic acid derivatives, N-vinyl compounds such as N-vinyl caprolactam, N-vinyl pyrrolidone, and N-vinyl formamide; aromatic vinyl compounds such as styrene and α-methyl styrene; vinyl ethers such as diethylene glycol divinyl ether, triethylene glycol divinyl ether, and cyclohexane dimethanol divinyl ether; and allyl compounds such as allyl glycidyl ether, diallyl phthalate, and triallyl trimellitate may also be used.

Acrylamide compounds free of the ester structure may also be used as other polymerizable compounds.

The content of the other polymerizable compounds than the acrylamide compound (A1) and the multifunctional polymerizable compound (A2) is preferably 1% by mass or greater but 30% by mass or less and more preferably 5% by mass or greater but 20% by mass or less relative to the total amount of the composition.

<Polymerization Initiator (B)>

The composition of the present disclosure may contain a polymerization initiator. The polymerization initiator may be referred to simply as initiator. As the polymerization initiator, there are a thermal polymerization initiator and a photopolymerization initiator.

The photopolymerization initiator may be any substance that can produce active species such as radicals and cations in response to the energy of active energy rays and initiate polymerization of a polymerizable compound (e.g., a monomer and an oligomer). As such a photopolymerization initiator, one, or two or more in combination, selected from, for example, known radical polymerization initiators, cationic polymerization initiators, and base generators may be used. Above all, radical polymerization initiators are preferable.

Examples of radical polymerization initiators include aromatic ketones, acylphosphine oxide compounds, aromatic onium salt compounds, organic peroxides, thio compounds (e.g., thioxanthone compounds and thiophenyl group-containing compounds), hexaaryl biimidazole compounds, ketoxime ester compounds, borate compounds, adinium compounds, metallocene compounds, active ester compounds, carbon-halogen bond-containing compounds, and alkylamine compounds.

The radical polymerization initiator is not particularly limited and may be appropriately selected depending on the intended purpose. Examples of the radical polymerization initiator include polyethylene glycol 200-di(β-4(4-(2-dimethylamino-2-benzyl)butanonylphenyl)piperazine) (available from IGM, "OMNIPOL 910"), 1,3-di({α-[1-chloro-9-oxo-9H-thioxanthen-4-yl)oxy]acetyl poly[oxy(1-methylethylene)]}oxy)-2,2-bis({α-[1-chloro-9-oxo-9H-thioxanthen-4-yl)o xy]acetyl poly [oxy(1-methylethylene)]}oxymethyl)propane (available from Lambson Limited, "SPEEDCURE 7010"), a mixture of 1,3-di({x-4-(dimethylamino) benzoyl poly[oxy(1-methylethylene)]}oxy)-2,2-bis({α-4-(dimethylamino)benzoyl poly[oxy(1-methylethylene)]} oxymethyl)propane with {α-4-(dimethylamino)benzoyl poly(oxyethylene)-poly[oxy(1-methylethylene)]-poly(oxyethylene)}4-(dimethylamino) benzoate (available from Lambson Limited, "SPEEDCURE 7040"), polybutylene glycol bis(9-oxo-9H-thioxanthinyloxy) acetate (available from IGM, "OMNIPOL TX"), a polymeric thioxanthene compound (available from Rahn AG, "GENOPOL TX-2"), and oligomers of 2-hydroxy-1-(4-isopropenylphenyl)-2-methylpropan-1-one [benzene, (1-methylethynyl)-, homopolymers, and ar(2-hydroxy-2-methyl-1-oxopropyl) derivatives] (available from IGM, "ESACURE ONE"). One of these radical polymerization initiators may be used alone or two or more of these radical polymerization initiators may be used in combination.

The content of the polymerization initiator is preferably 1% by mass or greater but 20% by mass or less, preferably 3% by mass or greater but 15% by mass or less, and preferably 5% by mass or greater but 10% by mass or less relative to the total amount of the composition in terms of obtaining a sufficient curing speed.

In addition to the polymerization initiator, a polymerization promotor (sensitizer) may also be used in combination. The polymerization promotor is not particularly limited. Examples of the polymerization promotor include amine compounds such as trimethylamine, methyl dimethanolamine, triethanolamine, p-diethylaminoacetophenone, ethyl p-dimethyl aminobenzoate, p-dimethylamino benzoic acid-2-ethyl hexyl, N,N-dimethyl benzyl amine, and 4,4'-bis(diethylamino)benzophenone.

The content of the polymerization promotor is not particularly limited and may be appropriately set depending on the polymerization initiator used and the amount of the polymerization initiator.

The composition of the present disclosure may further contain a polymerization inhibitor. This can increase the storage property (storage stability) of the composition. This also makes it possible to prevent clogging of a head due to thermal polymerization, in the case of discharging the composition by heating the composition and decreasing the viscosity of the composition.

The polymerization inhibitor is not particularly limited and may be appropriately selected depending on the intended purpose. Examples of the polymerization inhibitor include hydroquinone, benzoquinone, p-methoxyphenol, TEMPO, TEMPOL, and aluminum-cupferron complex. The content of the polymerization inhibitor is preferably 200 ppm or greater but 20,000 ppm or less relative to the total amount of the composition.

<Colorant>

The composition of the present disclosure may contain a colorant. As the colorant, various pigments and dyes may be used that impart black, white, magenta, cyan, yellow, green, orange, and gloss colors such as gold and silver, depending on the intended purpose of the composition and requisite properties thereof.

A content of the colorant in the composition is not particularly limited, and may be appropriately determined considering, for example, a desired color density and dispersibility of the colorant in the composition. However, it is preferably from 0.1% by mass to 20% by mass relative to the total mass of the composition. Incidentally, the composition of the present disclosure does not necessarily contain a colorant but can be clear and colorless. In such a case, for example, such a clear and colorless composition is good for an overcoating layer to protect an image.

The pigment can be either inorganic or organic, and two or more of the pigments can be used in combination.

Specific examples of the inorganic pigments include, but are not limited to, carbon blacks (C.I. Pigment Black 7) such as furnace black, lamp black, acetylene black, and channel black, iron oxides, and titanium oxides.

Specific examples of the organic pigments include, but are not limited to, azo pigments such as insoluble azo pigments, condensed azo pigments, azo lakes, and chelate azo pigments, polycyclic pigments such as phthalocyanine pigments, perylene pigments, perinone pigments, anthraquinone pigments, quinacridone pigments, dioxane pigments, thioindigo pigments, isoindolinone pigments, and quinofuranone pigments, dye chelates (e.g., basic dye chelates, acid dye chelates), dye lakes (e.g., basic dye lakes, acid dye lakes), nitro pigments, nitroso pigments, aniline black, and daylight fluorescent pigments.

In addition, a dispersant is optionally added to enhance the dispersibility of pigment. The dispersant has no particular limit and can be, for example, polymer dispersants conventionally used to prepare pigment dispersion (material).

The dyes include, for example, acidic dyes, direct dyes, reactive dyes, basic dyes, and combinations thereof.

<Organic Solvent>

The composition of the present disclosure optionally contains an organic solvent although it is preferable to spare it. The composition free of an organic solvent, in particular volatile organic compound (VOC), is preferable because it enhances safety at where the composition is handled and makes it possible to prevent pollution of the environment. Incidentally, the organic solvent represents a conventional non-reactive organic solvent, for example, ether, ketone, xylene, ethyl acetate, cyclohexanone, and toluene, which is clearly distinguished from reactive monomers. Furthermore, "free of" an organic solvent means that no organic solvent is substantially contained. The content thereof is preferably less than 0.1 percent by mass.

<Other Components>

The composition of the present disclosure optionally contains other components. The other components are not particularly limited and may be appropriately selected depending on the intended purpose. Specific examples thereof include, but are not limited to, a plasticizer, a thickener, a fungicide, a preservative, an fiber reinforcing material, a stabilizer, a surfactant, a leveling agent, a defoaming agent, a fluorescent brightener, a permeation enhancing agent, a wetting agent (humectant), a fixing agent, a viscosity stabilizer, an antioxidant, an ultraviolet absorbent, a chelate agent, and a pH adjuster.

The plasticizer can impart flexibility to a polymer formed of a monomer. Examples of the plasticizer include polyethylene glycol ester, terminally capped polyester, butyl stearate, lauric acid, dioctyl glutarate, triglyceride, dioctyl oxalate, triethyl phosphate, and acetyl tributyl citrate.

Examples of the thickener include polycyano acrylate, polylactic acid, polyglycolic acid, polycaprolactone, polyacrylic acid alkyl ester, and polymethacrylic acid alkyl ester.

Examples of the antiseptic include hitherto used substances that do not cause a monomer to initiate polymerization, such as potassium sorbate, sodium benzoate, sorbic acid, and chlorocresol.

The fiber reinforcing material is not particularly limited. Examples of the fiber reinforcing material include natural rubbers or synthetic rubbers such as styrene and acrylonitrile for reinforcing shock resistance of the composition.

The stabilizer performs the function of suppressing polymerization of a monomer during storage. Examples of the stabilizer include anionic stabilizers and free radical stabilizers. Examples of the former include metaphosphoric acid, maleic acid, maleic anhydride, alkyl sulfonic acid, phosphorus pentoxide, iron (III) chloride, antimony oxide, 2,4,6-trinitrophenol, thiol, alkyl sulfonyl, alkyl sulfone, alkyl sulfoxide, alkyl sulfite, sultone, sulfur dioxide, and sulfur trioxide. Examples of the latter include hydroquinone, catechol, and derivatives of these substances.

<Preparation of Composition>

The composition of the present disclosure can be prepared by using the components described above. The preparation devices and conditions are not particularly limited. For example, the composition can be prepared by subjecting the acrylamide compound (A1), the multifunctional polymerizable compound (A2), a pigment, a dispersant, etc., to a dispersion treatment using a dispersing machine such as a ball mill, a kitty mill, a disk mill, a pin mill, and a DYNO-MILL to prepare a pigment liquid dispersion, and further mixing the pigment liquid dispersion with a polymerization initiator, a polymerization inhibitor and a surfactant.

<Viscosity>

The viscosity of the composition of the present disclosure has no particular limit because it can be adjusted depending on the purpose and application devices. For example, if an ejecting device that ejects the composition from nozzles is employed, the viscosity thereof is preferably in the range of 3 mPa·s to 40 mPa·s, more preferably 5 mPa·s to 15 mPa·s, and particularly preferably 6 mPa·s to 12 mPa·s in the temperature range of 20 degrees C. to 65 degrees C., preferably at 25 degrees C. In addition, it is particularly preferable to satisfy this viscosity range by the composition free of the organic solvent described above. Incidentally, the viscosity can be measured by a cone plate rotary viscometer (VISCOMETER TVE-22L, manufactured by TOKI SANGYO CO., LTD.) using a cone rotor (1°34'×R24) at a number of rotation of 50 rpm with a setting of the temperature of hemathermal circulating water in the range of 20 degrees C. to 65 degrees C. VISCOMATE VM-150III can be used for the temperature adjustment of the circulating water.

<Curing Unit>

Examples of a curing unit configured to cure the composition of the present disclosure include thermal curing or curing by active energy rays. Of these units, curing by active energy rays is preferable.

Active energy rays used for curing the composition of the present disclosure are not particularly limited, so long as they are able to give necessary energy for allowing polymerization reaction of polymerizable components in the composition to proceed. Examples of the active energy rays include electron beams, $\alpha$-rays, $\beta$-rays, $\gamma$-rays, and X-rays, in addition to ultraviolet rays. When a light source having a particularly high energy is used, polymerization reaction can be allowed to proceed without a polymerization initiator. In addition, in the case of irradiation with ultraviolet ray, mercuryfree is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long time working life, high efficiency, and high cost performance make such irradiation sources desirable.

Above all, in terms of energy saving and device downsizing, ultraviolet rays emitted by an ultraviolet light-emitting diode (hereinafter, may also be referred to as UV-LED) and having a peak in a wavelength range of 285 nm or greater but 405 nm or less (preferably, 365 nm or greater but 405 nm or less) are preferable. Generally, the light absorption spectrum of polymerization initiators is broad, and use of UV-LED configured to emit a narrow specific wavelength range makes it difficult to improve the curability of compositions. Hence, use of the composition of the present disclosure excellent in curability even if UV-LED is used is preferable.

<Application Field>

The application field of the composition of the present disclosure is not particularly limited. It can be applied to any field where active-energy-ray-curable compositions are used. For example, the composition is selected to a particular application and used for a resin for processing, a paint, an adhesive, an insulant, a releasing agent, a coating material, a sealing material, various resists, and various optical materials. Furthermore, the composition of the present disclosure can be used to form two-dimensional texts, images, and designed coating film on various substrates and in addition used as a solid object forming material to form a three-dimensional object. This three dimensional object forming material may also be used as a binder for powder particles used in a powder layer laminating method of forming a three-dimensional object by repeating curing and layer-forming of powder layers, and as a three-dimensional object constituent material (a model material) and a supporting member used in an additive manufacturing method (a stereolithography method) as illustrated in FIG. 1 and FIGS. 2A to 2D. FIG. 1 is a diagram illustrating a method of additive manufacturing (to be described in detail below) to sequentially form layers of the composition of the present disclosure one on top of the other by repeating discharging the composition to particular areas followed by curing upon irradiation of an active energy ray. FIGS. 2A to 2D are each a diagram illustrating a method of additive manufacturing to sequentially form cured layers 6 having respective predetermined forms one on top of the other on a movable stage 3 by irradiating a storing pool (storing part) 1 of the composition 5 of the present disclosure with the active energy ray 4.

An apparatus for fabricating a three-dimensional object by the composition of the present disclosure is not particularly limited and can be a known apparatus. For example, the apparatus includes a containing device, a supplying device, and a discharging device of the composition, and an active energy ray irradiator. In addition, the present disclosure includes cured materials obtained by curing the composition and processed products obtained by processing structures having the cured materials on a substrate. The processed product is fabricated by, for example, heat-drawing and punching a cured material or structure having a sheet-like form or film-like form. Examples thereof are gauges or operation panels of vehicles, office machines, electric and electronic machines, and cameras.

The substrate is not particularly limited. It can suitably be selected to a particular application. Examples thereof include paper, thread, fiber, fabrics, leather, metal, plastic, glass, wood, ceramic, or composite materials thereof. Of these, plastic substrates are preferred in terms of processability.

Moreover, the composition of the present disclosure not only forms two-dimensional texts, images, and designed coating film on various substrates, but also, for example, a cured product obtained by curing the composition and an artificial nail formed by processing a structure having the cured product over a nail or a nail-shaped plastic base material. The composition of the present disclosure is particularly suitable as a base coat for an artificial nail composition, because the composition is excellent in removability and close adhesiveness with nails.

<<Stored Container>>

The stored container of the present disclosure contains the composition and is suitable for the applications as described above. For example, a container that stores the composition of the present disclosure can be used as a composition cartridge or a composition bottle. Therefore, users can avoid direct contact with the composition during operations such as transfer or replacement of the composition, so that fingers and clothes are prevented from contamination. Furthermore, inclusion of foreign matters such as dust in the composition can be prevented. In addition, the container can be of any size, any form, and any material. For example, the container can be designed to a particular application. It is preferable to use a light blocking material to block the light or cover a container with a light blocking sheet, etc.

<<Image Forming Method and Forming Apparatus>>

In an image forming method of the present disclosure, a step of applying the composition of the present disclosure is not particularly limited, and examples include a coating tool such as a brush and a method for discharging the composition of the present disclosure. Examples of a curing step include active energy rays and heating. In order to cure the composition of the present disclosure with active energy rays, an irradiating step of irradiating the composition with active energy rays may be provided, an image forming apparatus of the present disclosure may include an irradiating unit configured to irradiate the composition with active energy rays and a storing part configured to store the composition of the present disclosure, and the container may be accommodated in the storing part. Further, a step of coating the composition of the present disclosure with a coating tool such as a brush and a coating unit, and a discharging step of discharging the composition of the present disclosure and a discharging unit may be provided. The discharging method is not particularly limited and examples of the discharging method include a continuous jetting method and an on-demand method. Examples of the on-demand method include a piezo method, a thermal method, and an electrostatic method.

FIG. 1 is a schematic diagram illustrating an example of the image forming apparatus (apparatus to fabricate a 3D object) of the present disclosure. An image forming apparatus 39 illustrated in FIG. 1 sequentially forms thin layers one on top of the other using a head unit having inkjet heads arranged movable in the directions indicated by the arrows A and B. In the image forming apparatus 39, an ejection head unit 30 for additive manufacturing ejects a first composition, and ejection head units 31 and 32 for support and curing these compositions eject a second composition having a different composition from the first composition, while ultraviolet irradiators 33 and 34 adjacent to the ejection head units 31 and 32 cure the compositions. To be more specific, for example, after the ejection head units 31 and 32 for support eject the second composition onto a substrate 37 for additive manufacturing and the second composition is solidified by irradiation of an active energy ray to form a first substrate layer having a pool for composition, the ejection head unit 30 for additive manufacturing ejects the first composition onto the pool followed by irradiation of an active energy ray for solidification, thereby forming a first additive manufacturing layer. This step is repeated multiple times lowering the stage 38 movable in the vertical direction to laminate the supporting layer and the additive manufacturing layer to fabricate a solid object 35. Thereafter, an additive manufacturing support 36 is removed, if desired. Although only a single ejection head unit 30 for additive manufacturing is provided to the image forming apparatus illustrated 39 in FIG. 1, it can have two or more units 30. Further, a hand or a finger may be put over the substrate 37 for additive manufacturing to form an image over a nail.

(Artificial Nail Composition, Nail Decoration Material, and Artificial Nail)

An artificial nail composition of the present disclosure contains the composition of the present disclosure and further contains other components as needed.

Additives such as a colorant (e.g., a pigment and a dye), an inorganic filler (e.g., metal powder, calcium carbonate, talc, silica, alumina, and aluminum hydroxide), a flame retardant, an organic filler, an antioxidant, a polymerization inhibitor, a defoaming agent, a coupling agent, a leveling agent, and a rheology control agent may be blended in an appropriate amount in the artificial nail composition of the present disclosure so long as the features of the present disclosure are not spoiled.

Examples of the nail decoration material include manicures, pedicures, sculptures, and gel nails used for decoration or reinforcement of nails.

Examples of the artificial nail include a fake nail formed of a synthetic resin over a nail (real nail).

The artificial nail composition of the present disclosure is a composition to be coated over a nail of a human or an animal or over any other artificial nail and cured by light exposure, to form an artificial nail. The artificial nail formed of the artificial nail composition of the present disclosure can be removed by a removing method using, for example, an organic solvent.

An artificial nail of the present disclosure refers to a layer formed over a nail of a human or an animal or over any other artificial nail with a view to decoration or protection, or both thereof. Further, examples of the any other artificial nail include an arbitrary-shaped resin base material (fake nail) for nail decoration or protection, or both thereof.

Note that "a nail of a human and an animal, and any other artificial nail" will also be referred to simply as "a nail".

The shape of the artificial nail is not particularly limited and may be a desired shape. For example, the artificial nail may be formed in a manner to coat the surface of a nail or may be formed over a part of a nail, or with the use of, for example, a nail form, may be formed in a shape larger than a nail for nail extension.

The thickness of the artificial nail composition of the present disclosure can be controlled by coating. The thickness of the entire artificial nail is not particularly limited so long as the thickness is in a range of typical thicknesses of artificial nails, and is preferably in a range of 10 micrometers or greater but 2,000 micrometers or less in terms of durability and removability.

For example, it is common that the configuration of an artificial nail is a layer structure including any one or more selected from, for example, in order of closeness to a nail, a primer layer (a layer between the nail and a base layer for improving an adhesive force with the nail when the adhesive force is insufficient only with the base layer), a base layer (a layer between the nail and a color layer for improving the adhesive force and preventing color migration to the nail), a color layer (a layer containing a colorant), and a top layer (an outermost layer for improving durability, gloss, and aesthetic appearance). The artificial nail composition of the present disclosure can be suitably used for any of a base layer or a color layer or a top layer, or all thereof.

Above all, in view of durability and removability, it is preferable that a layer obtained by curing the artificial nail composition of the present disclosure be in contact with a nail.

Moreover, separately, a primer layer or a base layer or a color layer or a top layer, or all thereof may be provided as an upper layer of an artificial nail layer formed of the artificial nail composition of the present disclosure (the upper layer being a surface at a side of the artificial nail layer opposite to the nail) or as a lower layer (a surface between the artificial nail layer and the nail) with a view to imparting a color or gloss or close adhesiveness, or all thereof.

The artificial nail composition of the present disclosure is a photocurable artificial nail composition (also referred to as "artificial nail composition for gel nail") as a nail decoration material, and is an artificial nail composition curable by active energy rays.

FIG. 3A is a schematic view illustrating an example of a nail decorating apparatus configured to decorate a human nail. FIG. 3B is an enlarged schematic view of a decorating unit of FIG. 3A.

In FIG. 3A, the reference numeral 101 denotes a decorating unit, the reference numeral 102 denotes a securing unit, the reference numeral 104 denotes a cover, and the reference numeral 105 denotes a human hand, which is the decoration target. In FIG. 3B, the reference numeral 110 denotes an ultraviolet lamp, the reference numeral 111 denotes an inkjet head, and the reference numeral 112 denotes an enlarged view of the decorating unit 101 equipped with a camera.

According to the nail decorating apparatus 100 illustrated in FIG. 3A and FIG. 3B, with the human hand, which is the decoration target, secured by means of the securing unit 102 and positioned in place by means of the camera 112, the artificial nail composition of the present disclosure is discharged from the inkjet head onto a nail, which is a decoration target, and irradiated with ultraviolet rays by means of the ultraviolet lamp 110. In this way, the nail can be decorated. The decorating unit 101 is movable in the directions of the arrows in FIG. 3A.

EXAMPLES

The present disclosure will be described below by way of Examples. The present disclosure should not be construed as being limited to these Examples.

<Constituent Components of Composition>

Abbreviations of materials and names of compounds used for composition preparation, manufacturer names, and product names are presented in Table 1.

Commercially unavailable materials were synthesized in the manners described in Synthesis examples 1 to 7. Identification of the synthesized compounds was performed by a nuclear magnetic resonance spectroscopy method (instrument used: "JNM-ECX500" available from JEOL Ltd.), and purity measurement was performed by a gas chromatograph method (instrument used: "GCMS-QP2010 PLUS" available from Shimadzu Corporation). These chemical analyses were performed according to the rule.

TABLE 1

| | Symbol | Name or structure of compound | Product name (manufacturer name) |
|---|---|---|---|
| Acrylamide compound (A1) | A1-1 | (structure) | see Synthesis example 1 |
| | A1-2 | (structure) | see Synthesis example 2 |
| | A1-3 | (structure) | see Synthesis example 3 |
| | A1-4 | (structure) | see Synthesis example 4 |
| | A1-5 | (structure) | see Synthesis example 5 |
| | A1-6 | (structure) | see Synthesis example 6 |
| | A1-7 | (structure) | see Synthesis example 7 |
| | A1-8 | Acryloylmorpholine (molecular weight: 141.2) | ACMO (available from KJ Chemicals Corporation) |
| | A1-9 | N,N',N''-triacryloyldiethylenetriamine (molecular weight: 265.3) | FAM-301 (available from FUJIFILM Corporation) |
| Multifunctional polymerizable compound (A2) | A2-1 | Caprolactone modified dipentaerythritol hexaacrylate (SP value: 9.8) | DPCA60 (available from Nippon Kayaku Co., Ltd.) |
| | A2-2 | Diethylene glycol dimethacrylate (SP value: 8.9) | 2G (available from Shin Nakamura Chemical Co. Ltd.) |
| | A2-3 | Urethane diacrylate oligomer (SP value: 10.8) | CN963 (available from Sartomer Compny Inc.) |
| | A2-4 | Dipentaerythritol hexaacrylate (SP value: 8.2) | DPHA (available from Daicel-Allnex Ltd.) |
| | A2-5 | Pentaerythritol tetraacrylate (SP value: 8.5) | PETA (available from Daicel-Allnex Ltd.) |

*Polymerization initiator: an oligomer of 2-hydroxy-1-(4-isopropenylphenyl)-2-methylpropan-1-on (available from IGM, "ESACURE ONE")
*Polymerization inhibitor: 4-methoxyphenol (available from Seiko Chemical Co., Ltd., product name: "METHOQUINONE")

Synthesis Example 1

<Synthesis of N-acryloyl-N-methyl glycine methyl ester (A1-1)>

N-methyl glycine methyl ester hydrochloride salt (available from Sigma-Aldrich Japan, reagent) (0.30 moles), potassium carbonate (available from Kanto Chemical Co., Inc., reagent) (0.45 moles), and water (400 mL) were stirred and mixed at from 0 degrees C. through 10 degrees C., and with that temperature maintained, acrylic acid chloride (available from Wako Pure Chemical Industries, Ltd., reagent) (0.33 moles) was slowly dropped to the resultant. After dropping was completed, the resultant was subjected to extraction three times with ethyl acetate (available from Kanto Chemical Co., Inc., reagent) (400 mL), and together with the ethyl acetate layer, the resultant was washed once with water (400 mL). Ethyl acetate was evaporated at a reduced pressure at 40 degrees C. to obtain the intended N-acryloyl-N-methyl glycine methyl ester (A1-1) (0.20 moles) in the form of an almost colorless, transparent liquid. The purity was 98.3% by mass.

N-acryloyl-N-methyl glycine methyl ester (A1-1) has a molecular weight of 157.2, and is a publicly known compound (CAS registration No. 72065-23-7).

Synthesis Example 2

<Synthesis of N-acryloyl-N-isopropylglycine isopropyl ester (A1-2)>

An intended N-acryloyl-N-isopropyl glycine isopropyl ester (A1-2) (0.22 moles) was obtained in the form of an almost colorless, transparent liquid in the same manner as in Synthesis Example 1, except that unlike in Synthesis Example 1, N-methyl glycine methyl ester hydrochloride salt was changed to N-isopropyl glycine isopropyl ester hydrochloride salt (available from Tokyo Chemical Industry Co., Ltd., reagent). The purity was 98.5% by mass.

N-acryloyl-N-isopropyl glycine isopropyl ester (A1-2) had a molecular weight of 213.2.

Synthesis Example 3

<Synthesis of N-acryloyl-N-isopropylglycine methyl ester (A1-3)>

An intended N-acryloyl-N-isopropylglycine methyl ester (A1-3) (0.22 moles) was obtained in the form of an almost colorless, transparent liquid in the same manner as in Synthesis Example 1, except that unlike in Synthesis Example 1, N-methyl glycine methyl ester hydrochloride salt was changed to N-isopropylglycine methyl ester hydrochloride salt (available from Tokyo Chemical Industry Co., Ltd., reagent). The purity was 98.5% by mass.

N-acryloyl-N-isopropylglycine methyl ester (A1-3) had a molecular weight of 185.2.

Synthesis Example 4

<Synthesis of N-acryloyl-N-methyl alanine methyl ester (A1-4)>

An intended N-acryloyl-N-methyl alanine methyl ester (A1-4) (0.22 moles) was obtained in the form of an almost colorless, transparent liquid in the same manner as in Synthesis Example 1, except that unlike in Synthesis Example 1, N-methyl glycine methyl ester hydrochloride salt was changed to N-methyl alanine methyl ester hydrochloride salt (available from Tokyo Chemical Industry Co., Ltd., reagent). The purity was 98.5% by mass.

N-acryloyl-N-methyl alanine methyl ester (A1-4) had a molecular weight of 171.2.

Synthesis Example 5

<Synthesis of N-acryloyl-N-methyl glycine isopropyl ester (A1-5)>

An intended N-acryloyl-N-methyl glycine isopropyl ester (A1-5) (0.22 moles) was obtained in the form of an almost colorless, transparent liquid in the same manner as in Synthesis Example 1, except that unlike in Synthesis Example 1, N-methyl glycine methyl ester hydrochloride salt was changed to N-methyl glycine isopropyl ester hydrochloride salt (available from Tokyo Chemical Industry Co., Ltd., reagent). The purity was 98.5% by mass.

N-acryloyl-N-methyl glycine isopropyl ester (A1-5) had a molecular weight of 185.2.

Synthesis Example 6

<Synthesis of N-acryloyl-N-methyl alanine isopropyl ester (A1-6)>

An intended N-acryloyl-N-methyl alanine isopropyl ester (A1-6) (0.22 moles) was obtained in the form of an almost colorless, transparent liquid in the same manner as in Synthesis Example 1, except that unlike in Synthesis Example 1, N-methyl glycine methyl ester hydrochloride salt was changed to N-methyl alanine isopropyl ester hydrochloride salt (available from Tokyo Chemical Industry Co., Ltd., reagent). The purity was 98.5% by mass.

N-acryloyl-N-methyl alanine isopropyl ester (A1-6) had a molecular weight of 199.2.

Synthesis Example 7

<Synthesis of ethyl N-acryloyl piperidine-4-carboxylate (A1-7)>

An intended ethyl N-acryloyl piperidine-4-carboxylate (A1-7) (0.27 moles) was obtained in the form of an almost colorless, transparent liquid in the same manner as in Synthesis Example 1, except that unlike in Synthesis Example 1, N-methyl glycine methyl ester hydrochloride salt was changed to ethyl piperidine-4-carboxylate hydrochloride salt (available from Tokyo Chemical Industry Co., Ltd., reagent). The purity was 99.2% by mass.

Ethyl N-acryloyl piperidine-4-carboxylate (A1-7) has a molecular weight of 211.3, and is a publicly known compound (CAS registration No. 845907-79-1).

Example 1

<Production of composition>

A1-1 (69.9% by mass), A2-1 (20.0% by mass), a polymerization initiator (ESACURE ONE, available from IGM) (10.0% by mass), and a polymerization inhibitor (METHOQUINONE, available from Seiko Chemical Co., Ltd.) (0.1% by mass) were added together in this order and stirred for 2 hours. After it was confirmed by visual observation that there was no undissolved content left, the resultant was filtrated through a membrane filter to remove coarse particles, to produce a composition of Example 1.

Examples 2 to 17 and Comparative Examples 1 to 8

Compositions of Examples 2 to 17 and Comparative Examples 1 to 8 were produced in the same manner as in Example 1, except that unlike in Example 1, the constituent components and contents (% by mass) were changed as presented in Table 2 to Table 4 below.

TABLE 2

|  |  | Ex. | | | | | | | |
| --- | --- | --- | --- | --- | --- | --- | --- | --- | --- |
|  |  | 1 | 2 | 3 | 4 | 5 | 6 | 7 | 8 |
| Acrylamide compound (A1) | A1-1 | 69.9 |  |  |  |  |  |  | 69.9 |
|  | A1-2 |  | 69.9 |  |  |  |  |  |  |
|  | A1-3 |  |  | 69.9 |  |  |  |  |  |
|  | A1-4 |  |  |  | 69.9 |  |  |  |  |
|  | A1-5 |  |  |  |  | 69.9 |  |  |  |
|  | A1-6 |  |  |  |  |  | 69.9 |  |  |
|  | A1-7 |  |  |  |  |  |  | 69.9 |  |
|  | A1-8 |  |  |  |  |  |  |  |  |
|  | A1-9 |  |  |  |  |  |  |  |  |
| Multifunctional polymerizable compound (A2) | A2-1 | 20.0 | 20.0 | 20.0 | 20.0 | 20.0 | 20.0 | 20.0 |  |
|  | A2-2 |  |  |  |  |  |  |  | 20.0 |
|  | A2-3 |  |  |  |  |  |  |  |  |
|  | A2-4 |  |  |  |  |  |  |  |  |
|  | A2-5 |  |  |  |  |  |  |  |  |
| Polymerization initiator | ESACUREONE | 10.0 | 10.0 | 10.0 | 10.0 | 10.0 | 10.0 | 10.0 | 10.0 |
| Polymerization inhibitor | METHOQUINONE | 0.1 | 0.1 | 0.1 | 0.1 | 0.1 | 0.1 | 0.1 | 0.1 |
| Total (% by mass) |  | 100.0 | 100.0 | 100.0 | 100.0 | 100.0 | 100.0 | 100.0 | 100.0 |

TABLE 3

|  |  | Ex. | | | | | | | | |
| --- | --- | --- | --- | --- | --- | --- | --- | --- | --- | --- |
|  |  | 9 | 10 | 11 | 12 | 13 | 14 | 15 | 16 | 17 |
| Acrylamide compound (A1) | A1-1 | 69.9 | 54.9 | 74.9 | 69.9 | 69.9 | 59.9 | 64.9 | 69.9 | 69.9 |
|  | A1-2 |  |  |  |  |  |  |  |  |  |
|  | A1-3 |  |  |  |  |  |  |  |  |  |
|  | A1-4 |  |  |  |  |  |  |  |  |  |
|  | A1-5 |  |  |  |  |  |  |  |  |  |
|  | A1-6 |  |  |  |  |  |  |  |  |  |
|  | A1-7 |  |  |  |  |  |  |  |  |  |
|  | A1-8 |  |  |  |  |  |  |  |  |  |
|  | A1-9 |  |  |  |  |  |  |  |  |  |
| Multifunctional polymerizable compound (A2) | A2-1 |  | 35.0 | 15.0 |  |  | 10.0 |  |  |  |
|  | A2-2 |  |  |  |  |  | 20.0 | 15.0 | 10.0 | 10.0 |
|  | A2-3 | 20.0 |  |  |  | 20.0 |  | 10.0 |  |  |
|  | A2-4 |  |  |  | 20.0 |  |  |  | 10.0 |  |
|  | A2-5 |  |  |  |  | 20.0 |  |  |  | 10.0 |
| Polymerization initiator | ESACUREONE | 10.0 | 10.0 | 10.0 | 10.0 | 10.0 | 10.0 | 10.0 | 10.0 | 10.0 |
| Polymerization inhibitor | METHOQUINONE | 0.1 | 0.1 | 0.1 | 0.1 | 0.1 | 0.1 | 0.1 | 0.1 | 0.1 |
| Total (% by mass) |  | 100.0 | 100.0 | 100.0 | 100.0 | 100.0 | 100.0 | 100.0 | 100.0 | 100.0 |

TABLE 4

|  |  | Comp. Ex. | | | | | | | |
| --- | --- | --- | --- | --- | --- | --- | --- | --- | --- |
|  |  | 1 | 2 | 3 | 4 | 5 | 6 | 7 | 8 |
| Acrylamide compound (A1) | A1-1 | 89.9 | 79.9 | 44.9 | 34.9 | 44.9 | 44.9 |  |  |
|  | A1-2 |  |  |  |  |  |  |  |  |
|  | A1-3 |  |  |  |  |  |  |  |  |
|  | A1-4 |  |  |  |  |  |  |  |  |
|  | A1-5 |  |  |  |  |  |  |  |  |
|  | A1-6 |  |  |  |  |  |  |  |  |
|  | A1-7 |  |  |  |  |  |  |  |  |
|  | A1-8 |  |  |  |  |  |  | 69.9 |  |
|  | A1-9 |  |  |  |  |  |  |  | 69.9 |
| Multifunctional polymerizable compound (A2) | A2-1 |  | 14.0 | 37.0 | 55.0 |  |  | 20.0 | 20.0 |
|  | A2-2 |  |  |  |  | 37.0 |  |  |  |
|  | A2-3 |  |  |  |  |  | 37.0 |  |  |
|  | A2-4 |  |  |  |  |  |  |  |  |
|  | A2-5 |  |  |  |  |  |  |  |  |

TABLE 4-continued

|  |  | Comp. Ex. | | | | | | | |
| --- | --- | --- | --- | --- | --- | --- | --- | --- | --- |
|  |  | 1 | 2 | 3 | 4 | 5 | 6 | 7 | 8 |
| Polymerization initiator | ESACUREONE | 10.0 | 10.0 | 10.0 | 10.0 | 10.0 | 10.0 | 10.0 | 10.0 |
| Polymerization inhibitor | METHOQUINONE | 0.1 | 0.1 | 0.1 | 0.1 | 0.1 | 0.1 | 0.1 | 0.1 |
| Total (% by mass) | | 100.0 | 100.0 | 100.0 | 100.0 | 100.0 | 100.0 | 100.0 | 100.0 |

<Production of Artificial Nails>

Each of the compositions obtained was applied over a plastic base material molded in a nail shape and irradiated with active energy rays having a light intensity of 10,000 mJ/cm² using an active energy ray irradiator (LIGHT HAMMER 6 D VALVE, available from Heraeus Holding GmbH), to produce artificial nails.

<Evaluation of Removability>

Each of the artificial nails obtained (i.e., the plastic base materials and cured products formed over the surface of the plastic base materials) was immersed in acetone for 10 minutes. Subsequently, removability of the cured layer over the taken-out artificial nail from the base material was evaluated according to the evaluation criteria described below. The results are presented in Table 5 to Table 7.

<Evaluation Criteria>

A: The cured film was able to be removed easily (the cured film was swollen).

B: The cured film was able to be removed although it took time to remove the cured film (the cured film was swollen slightly).

C: The cured film was unable to be removed or was completely dissolved (the composition was not practically usable because the cured film was not swollen, or was dissolved to cause the possibility that acetone would directly contact the nail or skin).

<Evaluation of Close Adhesiveness with Nails>

Each of the compositions obtained was directly applied over the surface of a nail and cured by irradiation of active energy rays having a light intensity of 3,000 mJ/cm² using an active energy ray irradiator (LIGHT HAMMER 6 D VALVE, available from Heraeus Holding GmbH), to obtain a cured product. After two weeks of living daily life in this state, the cured product formed over the surface of the nail was observed visually, to evaluate close adhesiveness with the nail according to the criteria described below. The results are presented in Table 5 to Table 7.

<Evaluation Criteria>

A: Almost no peeling was observed.

B: Peeling of 10% or greater but less than 30% was observed.

C: Peeling of 30% or greater was observed.

TABLE 5

|  | Ex. 1 | Ex. 2 | Ex. 3 | Ex. 4 | Ex. 5 | Ex. 6 | Ex. 7 | Ex. 8 |
| --- | --- | --- | --- | --- | --- | --- | --- | --- |
| Removability | A | A | A | A | A | A | A | A |
| Close adhesiveness with nail | A | A | A | A | A | A | A | A |

TABLE 6

|  | Ex. 9 | Ex. 10 | Ex. 11 | Ex. 12 | Ex. 13 | Ex. 14 | Ex. 15 | Ex. 16 | Ex. 17 |
| --- | --- | --- | --- | --- | --- | --- | --- | --- | --- |
| Removability | B | B | B | B | B | A | A | A | A |
| Close adhesiveness with nail | A | B | A | A | A | A | A | A | A |

TABLE 7

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
| --- | --- | --- | --- | --- | --- | --- | --- | --- |
| Removability | C | C | C | C | C | C | C | C |
| Close adhesiveness with nail | A | A | B | C | B | A | A | C |

Aspects of the present disclosure are, for example, as follows.

<1> A composition including:

an acrylamide compound (A1) having a molecular weight of 150 or greater but 250 or less; and a multifunctional polymerizable compound (A2), wherein a content of the multifunctional polymerizable compound (A2) is 15% by mass or greater but 35% by mass or less.

<2> The composition according to <1>, wherein the acrylamide compound (A1) is represented by at least any one selected from the group consisting of general formulae (1) and (2) below,

[Chem. 3]

General formula (1)

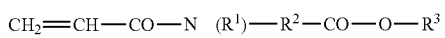

where in the general formula (1), $R^1$ represents a hydrogen atom, or a straight-chain or branched alkyl group containing 1 through 4 carbon atoms, $R^2$ represents a straight-chain or branched alkylene group containing 1 through 4 carbon atoms, $R^3$ represents a straight-chain or branched alkyl group containing 1 through 4 carbon atoms, and a total number of carbon atoms in $R^1$, $R^2$, and $R^3$ is 2 through 6,

[Chem. 4]

General formula (2)

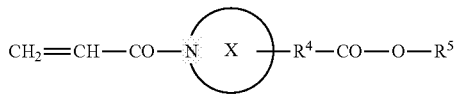

where in the general formula (2), a ring X represents a nitrogen atom-containing ring structure containing 2 through 5 carbon atoms, $R^4$ represents a single bond, or a straight-chain or branched alkylene group containing 1 through 3 carbon atoms, $R^5$ represents a straight-chain or branched alkyl group containing 1 through 3 carbon atoms, and a total number of carbon atoms in the ring X, $R^4$, and $R^5$ is 3 through 6.

<3> The composition according to <1> or <2>, wherein the multifunctional polymerizable compound (A2) contains 2 or more but 6 or less functional groups.

<4> The composition according to any one of <1> to <3>, wherein a content of the acrylamide compound (A1) is 20.0% by mass or greater but 98.0% by mass or less relative to a total amount of the composition.

<5> The composition according to any one of <1> to <4>, wherein a solubility parameter (SP value) of the multifunctional polymerizable compound (A2) is 10 (cal/cm$^3$)$^{0.5}$ or less.

<6> The composition according to any one of <1> to <5>, wherein the multifunctional polymerizable compound (A2) is at least one selected from the group consisting of dipentaerythritol hexa(meth)acrylate, caprolactone-modified dipentaerythritol hexa(meth)acrylate, pentaerythritol tetra(meth)acrylate, and diethylene glycol di(meth)acrylate.

<7> The composition according to any one of <1> to <6>, further including
a polymerization initiator.

<8> The composition according to any one of <1> to <7>, wherein the composition is free of an organic solvent.

<9> The composition according to any one of <1> to <8>, wherein the composition is an active-energy-ray-curable composition.

<10> A stored container including:
the composition according to any one of <1> to <9>; and
a container,
wherein the composition is stored in the container.

<11> A two-dimensional or three-dimensional image forming apparatus including:
a storing part configured to store the composition according to any one of <1> to <9>;
an applying unit configured to apply the composition; and
a curing unit configured to cure the composition.

<12> The image forming apparatus according to <11>, wherein the curing unit is a UV-LED configured to emit an ultraviolet ray having a peak in a wavelength range of 365 nm or greater but 405 nm or less.

<13> A two-dimensional or three-dimensional image forming method including:
applying the composition according to any one of <1> to <9>; and curing the composition.

<14> The image forming method according to <13>, wherein the curing includes irradiating the composition with an ultraviolet ray having a peak in a wavelength range of 365 nm or greater but 405 nm or less by a UV-LED.

<15> An artificial nail composition including
the composition according to any one of <1> to <9>.

<16> A nail decoration material including
the composition according to any one of <1> to <9>.

<17> An artificial nail including
a cured product of the composition according to any one of <1> to <9>.

The composition according to any one of <1> to <9>, the stored container according to <10>, the two-dimensional or three-dimensional image forming apparatus according to <11> or <12>, the two-dimensional or three-dimensional image forming method according to <13> or <14>, the artificial nail composition according to <15>, the nail decoration material according to <16>, and the artificial nail according to <17> can solve the various problems in the related art and can achieve the object of the present disclosure.

REFERENCE SIGNS LIST

1: storing pool (storing part)
3: movable stage
4: active energy ray
5: composition
6: cured layer
30: ejection head unit for additive manufacturing
31, 32: ejection head units for support
33, 34: ultraviolet irradiator
35: solid object
36: additive manufacturing support
37: substrate

The invention claimed is:
1. A composition comprising:
an acrylamide compound (A1) having a molecular weight of 150 or greater but 250 or less; and
a multifunctional polymerizable compound (A2),
wherein a solubility parameter (SP value) of the multifunctional polymerizable compound (A2) is 10 (cal/cm$^3$)$^{0.5}$ or less,
wherein a content of the multifunctional polymerizable compound (A2) is 15% by mass or greater but 35% by mass or less,
wherein a content of the acrylamide compound (A1) is 64.8% by mass or greater but 75% by mass or less,
wherein the acrylamide compound (A1) is represented by at least anyone selected from the group consisting of general formulae (1) and (2) below,

[Chem. 1]

General formula (1)

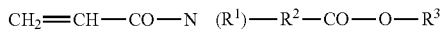

where in the general formula (1), $R^1$ represents a hydrogen atom, or a straight-chain or branched alkyl group that comprises 1 through 4 carbon atoms, $R^2$ represents a straight-chain or branched alkylene group that comprises 1 through 4 carbon atoms, $R^3$ represents a straight-chain or branched alkyl group that comprises 1 through 4 carbon atoms, and a total number of carbon atoms in $R^1$, $R^2$, and $R^3$ is 2 through 6,

[Chem. 2]

General formula (2)

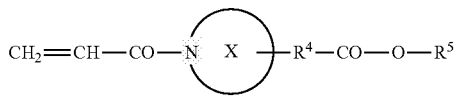

where in the general formula (2), a ring X represents a nitrogen atom-containing ring structure that comprises 2 through 5 carbon atoms, $R^4$ represents a single bond, or a straight-chain or branched alkylene group that comprises 1 through 3 carbon atoms, $R^5$ represents a straight-chain or branched alkyl group that comprises 1 through 3 carbon atoms, and a total number of carbon atoms in the ring X, $R^4$, and $R^5$ is 3 through 6.

2. The composition according to claim 1, wherein the multifunctional polymerizable compound (A2) comprises 2 or more but 6 or less functional groups.

3. The composition according to claim 1, wherein the multifunctional polymerizable compound (A2) comprises at least one selected from the group consisting of dipentaerythritol hexa(meth)acrylate, caprolactone-modified dipentaerythritol hexa(meth)acrylate, pentaerythritol tetra(meth)acrylate, and diethylene glycol di(meth)acrylate.

4. The composition according to claim 1, wherein the composition is an active-energy-ray-curable composition.

5. A container comprising:
the composition according to claim 1;
wherein the composition is stored in the container.

6. A two-dimensional or three-dimensional image forming method comprising:
applying the composition according to claim 1; and
curing the composition.

7. The image forming method according to claim 6, wherein the curing comprises irradiating the composition with an ultraviolet ray having a peak in a wavelength range of 365 nm or greater but 405 nm or less by a UV-LED.

8. An artificial nail composition comprising
the composition according to claim 1.

9. A nail decoration material comprising
the composition according to claim 1.

10. An artificial nail comprising
a cured product of the composition according to claim 1.

11. The composition according to claim 1, wherein the acrylamide compound (A1) is represented by a compound of the general formula (1).

* * * * *